United States Patent
Galvao et al.

(10) Patent No.: US 9,611,492 B2
(45) Date of Patent: Apr. 4, 2017

(54) USE OF VINASSE IN THE PROCESS OF SACCHARIFICATION OF LIGNOCELLULOSIC BIOMASS

(75) Inventors: Celia Maria Araujo Galvao, Americana (BR); Juliana Conceicao Teodoro, Piracicaba (BR); Liliane Pires Andrade, Piracicaba (BR); Jose Augusto Travassos Rios Tome, Piracicaba (BR); Oswaldo Godoy Neto, Piracicaba (BR)

(73) Assignee: CTC-Centro de Tecnologia Canavieira S.A., Santo Antonio (BR)

( * ) Notice: Subject to any disclaimer, the term of this patent is extended or adjusted under 35 U.S.C. 154(b) by 435 days.

(21) Appl. No.: 14/007,980

(22) PCT Filed: Mar. 5, 2012

(86) PCT No.: PCT/BR2012/000056
§ 371 (c)(1),
(2), (4) Date: Oct. 18, 2013

(87) PCT Pub. No.: WO2012/129622
PCT Pub. Date: Apr. 10, 2012

(65) Prior Publication Data
US 2014/0045237 A1 Feb. 13, 2014

(30) Foreign Application Priority Data

Mar. 30, 2011 (BR) ..................................... 1101295

(51) Int. Cl.
| C12P 7/10 | (2006.01) |
| C12P 19/00 | (2006.01) |
| C12P 7/08 | (2006.01) |
| C12N 1/38 | (2006.01) |
| C12P 19/14 | (2006.01) |
| C12F 3/10 | (2006.01) |

(52) U.S. Cl.
CPC ................ *C12P 19/00* (2013.01); *C12F 3/10* (2013.01); *C12N 1/38* (2013.01); *C12P 7/10* (2013.01); *C12P 19/14* (2013.01); *Y02E 50/16* (2013.01)

(58) Field of Classification Search
None
See application file for complete search history.

(56) References Cited

U.S. PATENT DOCUMENTS

| 5,914,040 | A * | 6/1999 | Pescher .................. C02F 1/444 210/638 |
| 7,807,419 | B2 | 10/2010 | Hennessey et al. |
| 2005/0136520 | A1* | 6/2005 | Kinley .................. C12M 21/12 435/155 |
| 2010/0086981 | A1 | 4/2010 | LaTouf et al. |
| 2010/0159515 | A1 | 6/2010 | Cirakovic |
| 2011/0262984 | A1* | 10/2011 | Nguyen .................. F23C 13/02 435/165 |

FOREIGN PATENT DOCUMENTS

| CN | 101838673 A | 9/2010 |
| EP | 048061 A2 | 3/1982 |
| EP | 0190610 A1 | 8/1986 |
| EP | 769915 A1 | 5/1997 |
| FR | 2697266 A1 | 4/1994 |
| RU | 2102480 C1 | 1/1998 |
| RU | 2208630 C1 | 7/2003 |
| WO | 2008040358 A1 | 4/2008 |
| WO | 2008116278 A1 | 10/2008 |
| WO | 2009155673 A1 | 12/2009 |
| WO | 2010100224 A1 | 9/2010 |

OTHER PUBLICATIONS

Mohagheghi et al_National Renewable Energy Laboratory_2009.*
Carmargo, O.A. et al., Bragantia, Campinas, 43(1):125-139, 1984.

* cited by examiner

*Primary Examiner* — Chris R Tate
*Assistant Examiner* — Douglas F White
(74) *Attorney, Agent, or Firm* — Laurence P. Colton; Smith Tempel Blaha LLC

(57) ABSTRACT

The use of stillage in a saccharification/fermentation process of lignocellulosic biomasses, regardless of the form of the biomasses and regardless of the use of the obtained final hydrolyzed broth. The beneficial effect conferred by the stillage to the saccharification process of lignocellulosic biomasses presents among other characteristics the ability to buffer the reaction medium, especially when such process takes place in an enzymatic route, but not limited to it, regardless of the type of biomass being used and the type of pretreatment to which the biomass is subjected. Fermentation processes, such as the ethanol production, using stillage as source of nutrients such as, for example, nitrogen, for growing microorganisms, but not limited to it.

3 Claims, 5 Drawing Sheets

USE OF VINASSE IN THE PROCESS OF SACCHARIFICATION OF LIGNOCELLULOSIC BIOMASS

FIELD OF THE INVENTION

The present invention relates to the use of stillage on saccharification/fermentation process of lignocellulosic biomasses, regardless of the form in which they present themselves and regardless of the destination given to the obtained final hydrolyzed broth. More specifically, the present invention describes the beneficial effect conferred by the stillage to the saccharification process of lignocellulosic biomasses, since it presents among other characteristics the ability to buffer the reaction medium, especially when such process takes place on enzymatic route, but not limited to it, regardless of the type of biomass being used and the type of pretreatment to which the biomass is subjected.

The present invention also relates to fermentation processes, such as the ethanol production, comprising the use of stillage as source of nutrients such as, for example, the nitrogen (N), for growing microorganisms, but not limited to it.

The present invention is in the chemical engineering area.

BACKGROUND OF THE INVENTION

The enzymatic hydrolysis process, especially the saccharification of lignocellulosic biomasses, takes place in general in buffered media or under controlled pH. Thus, it is common to use buffering solutions, such as for example, sodium citrate and sodium acetate, among others, or pH control solutions such as acids and bases (e.g. sodium hydroxide, hydrochloric acid, phosphoric acid and etc) so as to maintain the pH in an ideal value in which the saccharification process of these biomasses is favored. In general, the optimum operation pH of the system matches to the optimum operation pH of the enzymes responsible for the bioconversion process of the biomass into fermentable sugars. Cellulase, the most used enzymatic complex in the saccharification process of lignocellulosic biomasses, expresses its major activity in the pH range that ranges from 4.5 to 5.5. This pH range, besides favoring the catalytic process, also helps in maintaining the stability of the enzymatic complex for longer time periods, which extends the shelf life of the biocatalyst impacting beneficially and in a crucial manner the final cost of the process.

Conventional buffering solutions such as sodium citrate and sodium acetate are very expensive and can also make the productive process impossible to be done in certain situations. Acids and/or bases used for the pH control during the process despite presenting a significantly lower cost in relation to before mentioned solutions still represent a significant portion of the final cost of the process when compared to the process using stillage as the buffering agent. Thus, it the use of effective and cheap buffering agents becomes extremely desirable in the aforementioned process.

The use of stillage in the saccharification process of lignocellulosic biomasses presents many advantages when compared to conventional processes, but certainly an advantage of great importance is the significant savings on water consumption in the step of enzymatic hydrolysis of biomasses (pretreated or not), once the stillage can also substitute all necessary water in this specific process.

The presence of stillage in the enzymatic hydrolysis process of lignocellulosic biomasses allows the formation of chemical compounds which have the ability to promote the buffering effect of the reaction medium, that is, to maintain the pH inside a specific desirable range in order to provide a favorable environment to the suitable functioning of the enzymes making part of the enzymatic complex, which need well defined conditions to perform the breaking of bonds of their specific substrates, in order to maximize the generation of fermentable sugars from the lignocellulosic biomass used.

In the buffering process of the reaction medium, salts present in the stillage such as, for example, sodium, match to acids generated during the pretreatment process of the biomass, such as, for example, acetic acid, forming chemical compounds, such as for example, sodium acetate, which directly acts on the maintenance of the medium pH in certain ranges. Hence, the buffering effect arises from the chemical reaction which takes place between compounds naturally present in the stillage and in the pretreated biomass, dispensing thus the advance preparation of the buffering solution.

The present invention has as main advantages:
  greatly effective in the buffering of the reaction medium where the saccharification of lignocellulosic biomasses takes place, that is, the use of the stillage allows the pH of the suspension to be maintained in the optimum range of the enzymatic complex operation used (4.5-5.5), once biological catalysts express their major activity in a very strict range of the pH. Also, the maintenance of the pH in the optimum range of operation of the enzyme allows enzymes to maintain their stability for longer time periods, which extends the shelf life of the biocatalyst impacting in a beneficial and crucial way the final cost of the process;
  cheaper than conventional buffering solutions such as, for example, buffer solutions sodium citrate and sodium acetate, as the current is produced inside the industrial unit in great amounts since the equivalent for each liter of produced ethanol it is generated around 10 to 12 liters of stillage;
  rich in nitrogen, which is a macro nutrient of great importance in the fermentation process of sugars into ethanol, given that a typical industrial stillage can present until 1 g/L of total nitrogen in its composition; thus, besides cheapening the global cost of the process, the stillage still favors the specific step of fermenting hydrolyzed broths derived from the saccharification of sugar cane bagasse;
  suitable for use in the saccharification process of lignocellulosic biomasses also under an environmental viewpoint following the concept of closed cycle process, since this "residue" or "byproduct" is commonly used in the sugarcane fertigation process, being a very important source of soil and ground water pollution mainly due to its increasing high biochemical oxygen demand (BOD) in accordance with organic matter content present in its composition;
  allow water saving in the saccharification process of sugarcane bagasse substituting this one for the stillage.

In the patent scope, some relevant documents have been identified, which will be discussed hereinafter.

The document U.S. Pat. No. 7,807,419 discloses a process for saccharification of pretreated biomass in order to obtain high concentrations of fermentable sugars. Specifically, it is addressed to a process using a batch wise feeding system having a reduction in the size of particles. The present invention differs from this document by comprising the use of the stillage as the buffering agent of the saccharification reaction of biomasses, as well as the additive to fermentation due to the nitrogen content present in its composition.

The document US 2010/0086981 presents compositions and methods to improve the saccharification of biomasses with enzymes and modified microorganisms. Said document mentions the use of sodium citrate during the reaction. The present invention differs from this document by dispensing the use of sodium citrate, substituting it by the available stillage in large volumes in the sugar cane mills.

The document US 2010/0159515 describes a method of pretreatment of lignocellulosic biomasses mentioning the use of a buffer from citrates. The present invention differs from this document by using compounds present in the available stillage in the alcohol and sugar mills or independent distilleries to promote the buffering effect to the reaction medium.

The document WO 2008/040358 describes the use of a fermentation byproduct, the stillage, which is rich in potassium as the fertilizing agent. This document also says that the stillage rich in potassium is poor in amino acids and proteins, since the same have already been removed in previous steps. The present invention differs from this document by previewing the use of the stillage resulting from the industrial alcohol fermentation rich in nitrogen (to 1 g/L) not as the fertilizing agent, but as the buffering agent of the saccharification process of lignocellulosic biomasses; in addition, this stillage also shows itself suitable to the step of alcoholic fermentation, since it represents an additional source of nitrogen, essential macro nutrient to said fermentation process.

The document EP 048061 describes a process for recycling the stillage comprising the steps of concentration and burning of the stillage. However, nothing is said about its use in hydrolytic (acids or enzymatic) and/or fermentation processes; neither is about its characteristics as buffering agent or source of nitrogen.

The document WO 2008/116278 describes the stillage recycling as additive in animal feed, the stillage passing through a process of distillation and concentration, followed by dehydration.

The document EP 769915 describes the use of organic acids derived from the stillage; such compounds prove especially useful in microbial crops.

The present invention differs from this and from the other documents by using the stillage (or any residue/byproduct derived from the fermented wine distillation process) in any state of treatment (raw, filtered, concentrated, etc) as buffering agent of saccharification processes of lignocellulosic biomasses and fermentation additive (additional source of nitrogen).

What is known from the literature is that no documents were found previewing or suggesting the teachings of the present invention, in such a way that the solution proposed here is new and has inventive activity in relation to the state of the art.

SUMMARY OF THE INVENTION

The present invention describes the use of the stillage as the buffering agent of the saccharification processes of lignocellulosic biomasses and the additional source of nitrogen in fermentation processes, regardless of the source and the form in which such biomasses have been produced. In summary, the present invention has as the main competitive advantages the high efficiency, low cost and the preservation of the environment.

An object of the present invention is a saccharification process of lignocellulosic biomasses comprising the addition of the stillage (or any residue/byproduct derived from the process of fermented wine distillation) as the buffering agent to the reaction medium.

In a preferred embodiment, the enzymatic hydrolysis process is a saccharification process and it can occur under any selected configuration from the group comprising SHF (Separated Enzymatic hydrolysis and Fermentation), SSF (Simultaneous Enzymatic hydrolysis and Fermentation), SSCF (Enzymatic hydrolysis, Simultaneous Fermentation and Co-fermentation), CBP (Enzyme Production, Simultaneous Enzymatic hydrolysis and Fermentation), SEPHY (Enzyme Production and Enzymatic hydrolysis separated from the Fermentation) and combinations thereof.

It is a further object of the invention to provide a buffering agent made of stillage, which is useful in enzymatic hydrolysis processes.

It is a further object of the invention to provide the use of stillage as the buffering agent, comprising the step of collecting the stillage from the distillation process of wine resulting from the alcoholic fermentation process.

In another aspect, the present invention provides a fermentation process comprising the addition of a fermentation additive which is rich in nitrogen and essential to the fermentation process in question.

It is a further object of the present invention to provide a fermentation process comprising a step of fermentation in the presence of a fermentation additive made of stillage.

It is a further object of the present invention to provide an ethanol production process comprising the fermentation of sugars in the presence of a fermentation additive made of stillage.

It is a further object of the present invention to provide a fermentation additive made of stillage, which is useful as the source of nitrogen.

It is a further object of the present invention to provide a process of preparing fermentation additive comprising the step of collecting the stillage from the distillation process of wine resulting from the alcoholic fermentation process These and other objects of the invention will be immediately understood by those skilled in the art and by companies being interested in the segment and will be described in enough details for its reproduction in the description hereinafter.

(312) Pretreated biomass; (313) Hydrolysate; (314) Wine; (315) Stillage $1^{st}$ or $2^{nd}$ generation; and (316) Fertigation.

Figure 1:
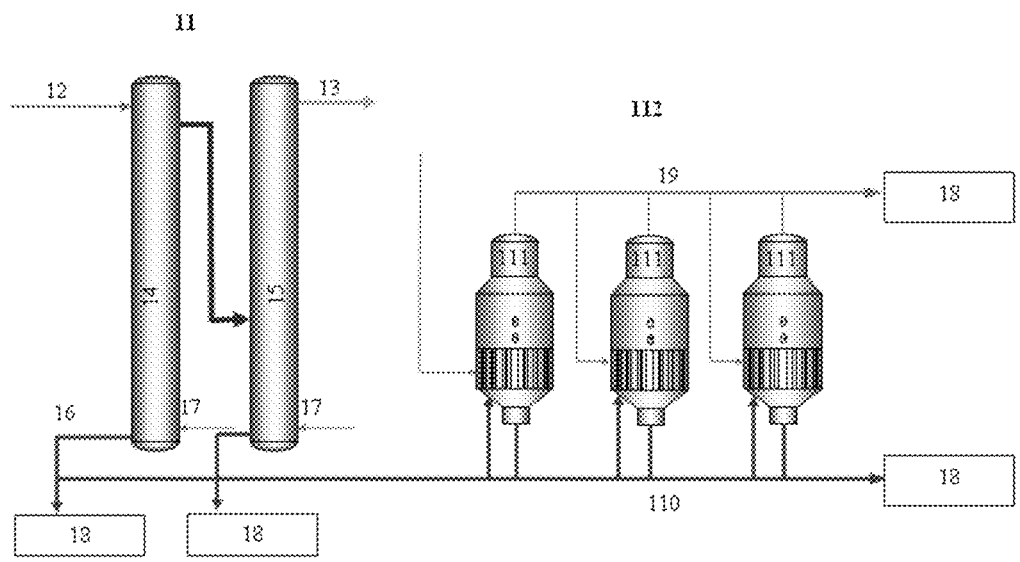
FIG. 1 discloses a possible flowchart of obtaining stillage for using it in the enzymatic hydrolysis. Keys: (11) Distillation; (12) Wine; (13) Ethanol; (14) Stripping; (15) Rectifying; (16) Stillage; (17) Vapor; (18) Enzymatic hydrolysis; (19) Condensate of stillage; (110) Concentrated stillage; (111) Evaporation; and (112) Concentration of stillage.
Figure 2:
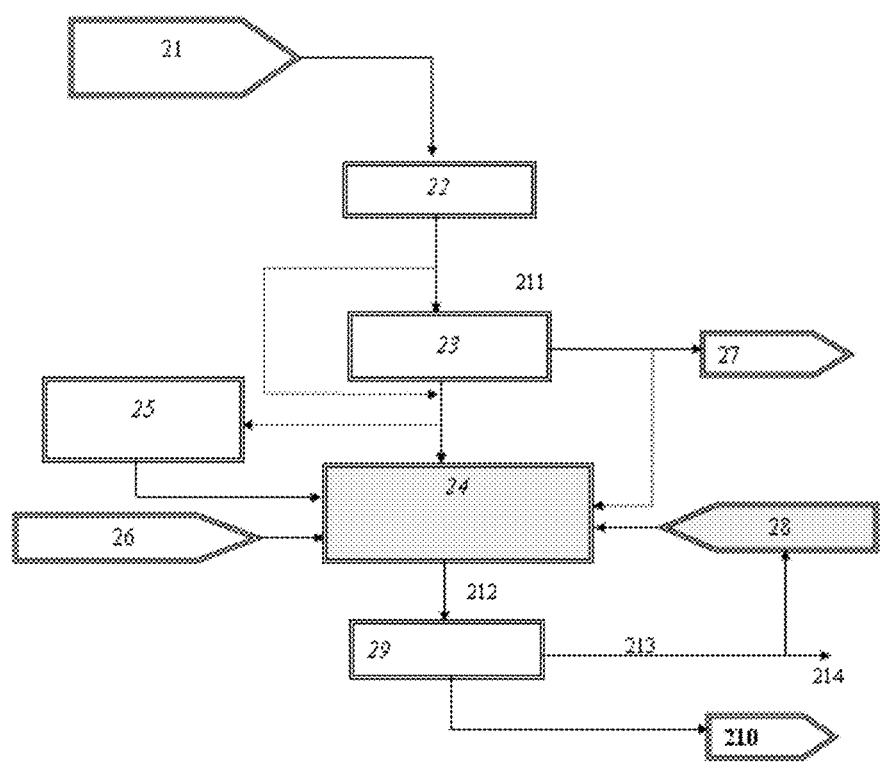
FIG. 2 discloses a flowchart of a possible saccharification route of lignocellulosic biomasses of the present invention—SSF: Enzymatic hydrolysis and Fermentation—simultaneous. Keys: (21) Lignocellulosic biomass; (22) Pretreatment; (23) Washing; (24) Enzymatic hydrolysis+Fermentation+Co-fermentation; (25) Enzyme production; (26) Microorganisms; (27) Sugars; (28) Stillage; (29) Purification; (210) Ethanol; (211) Pretreated biomass; (212) Wine; (213) Stillage $1^{st}$ or $2^{nd}$ generation; and (214) Fertigation.
Figure 3:
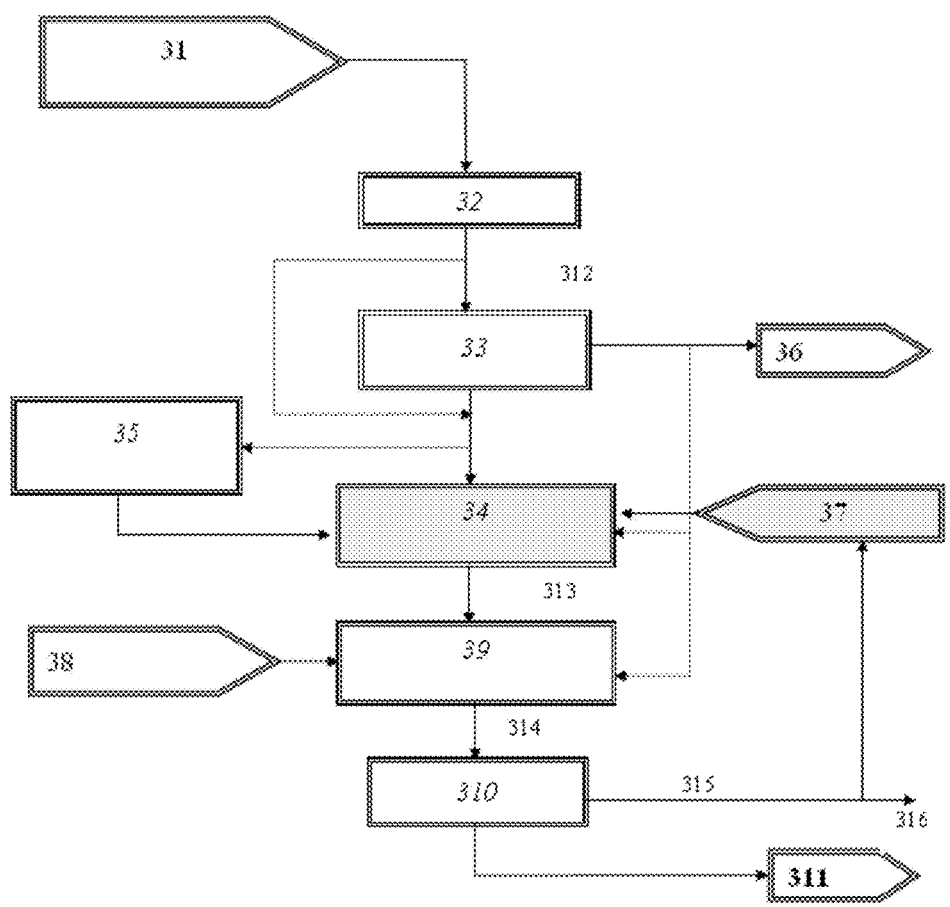
FIG. 3 discloses a flowchart of a possible saccharification route of lignocellulosic biomasses of the present invention—SHF: Enzymatic hydrolysis and Fermentation—separated. Keys: (31) Lignocellulosic biomass; (32) Pretreatment; (33) Washing; (34) Hydrolysis; (35) Enzyme production; (36) Sugars; (37) Stillage; (38) Microorganisms; (39) Fermentation/Co-fermentation; (310) Purification; (311) Ethanol.
Figure 4:
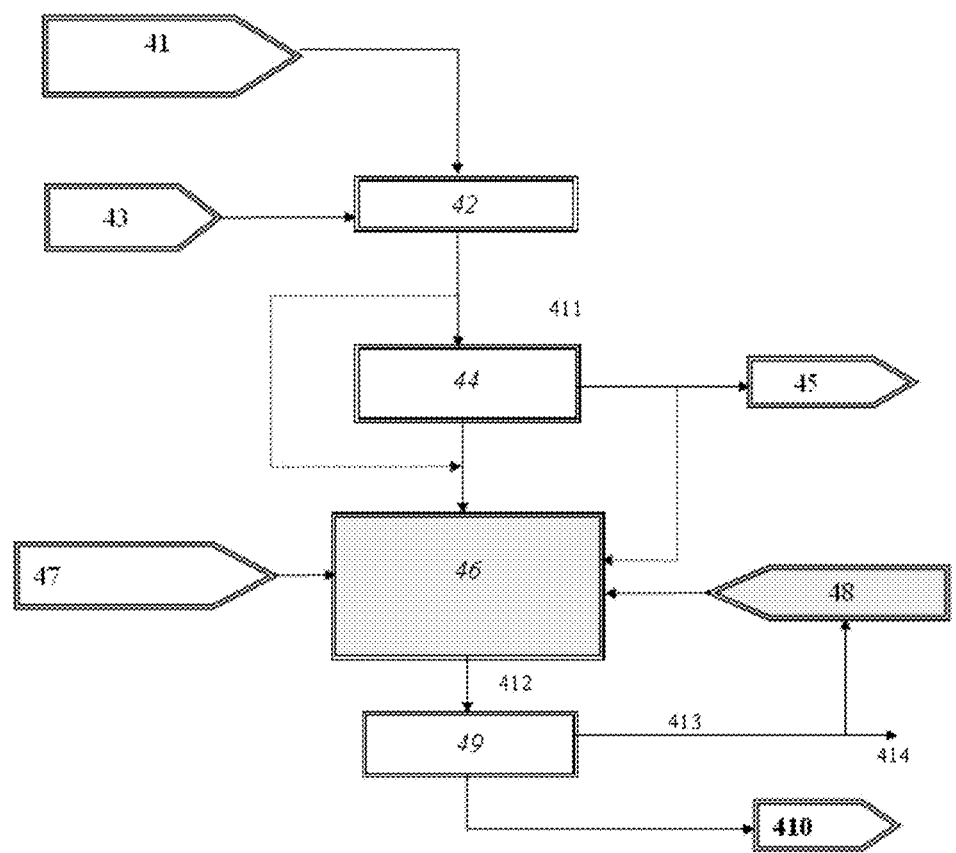

FIG. 4 discloses a flowchart of a possible saccharification route of lignocellulosic biomasses of the present invention—CBP: Enzyme production, Enzymatic hydrolysis and Fermentation—Simultaneous. Keys: (41) Lignocellulosic biomass; (42) Pretreatment; (43) Catalyst; (44) Washing; (45) Sugars; (46) Enzyme production+Enzymatic hydrolysis+Fermentation/Co-fermentation; (47) Microorganisms; (48) Stillage; (49) Purification; (410) Ethanol; (411) Pretreated biomass; (412) Wine; (413) Stillage $1^{st}$ or $2^{nd}$ generation; and (414) Fertigation.

Figure 5:
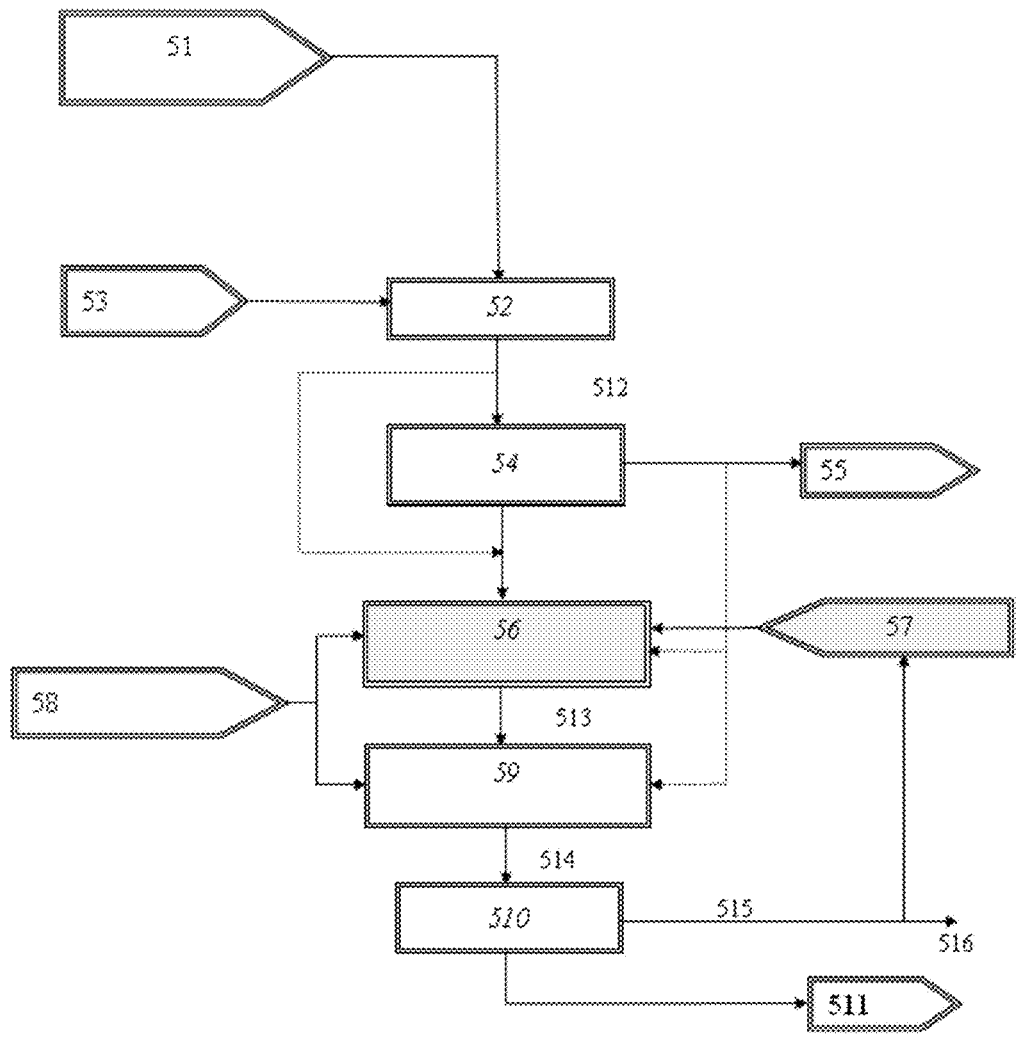

FIG. 5 discloses a flowchart of a possible saccharification route of lignocellulosic biomasses of the present invention—SEPHY: Enzyme production+Enzymatic hydrolysis separated from the Fermentation. Keys: (51) Lignocellulosic biomass; (52) Pretreatment; (53) Catalyst; (54) Washing; (55) Sugars; (56) Enzyme production+Enzymatic hydrolysis; (57) Stillage; (58) Microorganisms; (59) Fermentation/Co-fermentation; (510) Purification; (511) Ethanol; (512) Pretreated biomass; (513) Hydrolysate; (514) Wine; (515) Stillage $1^{st}$ or $2^{nd}$ generation; and (516) Fertigation.

Figure 6:
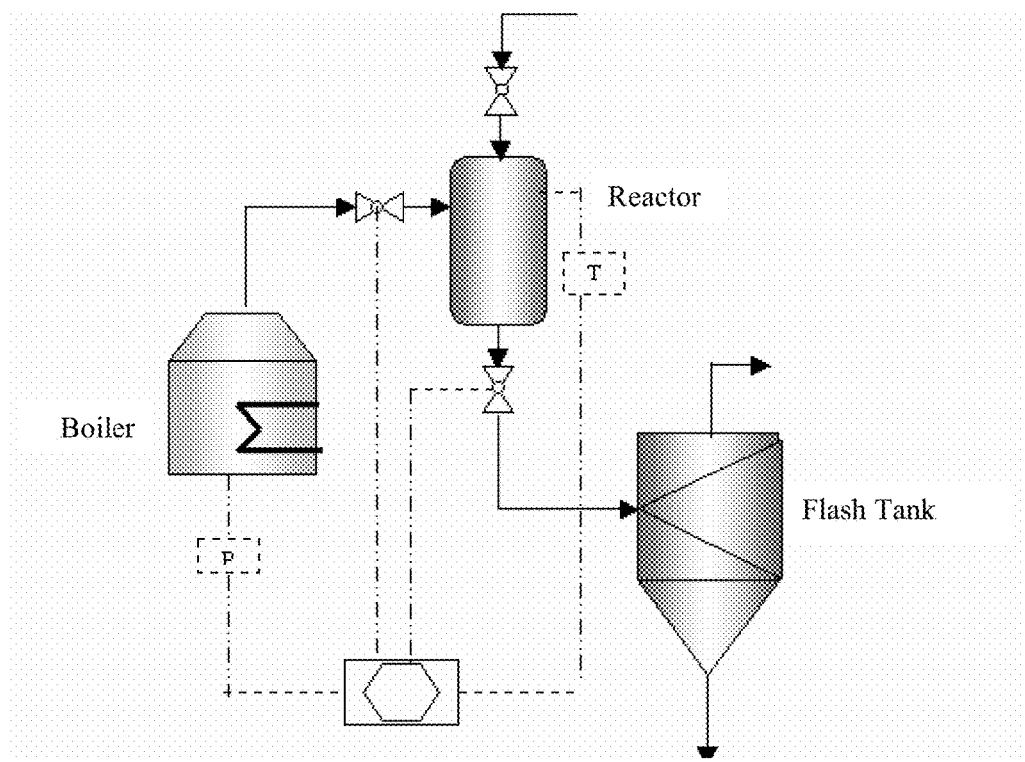

FIG. 6 is a schematic drawing of the pretreatment process of sugarcane bagasse with vapor (Steam Explosion) showing a boiler (steam generator), a reactor, and a flash tank.

Figure 7:
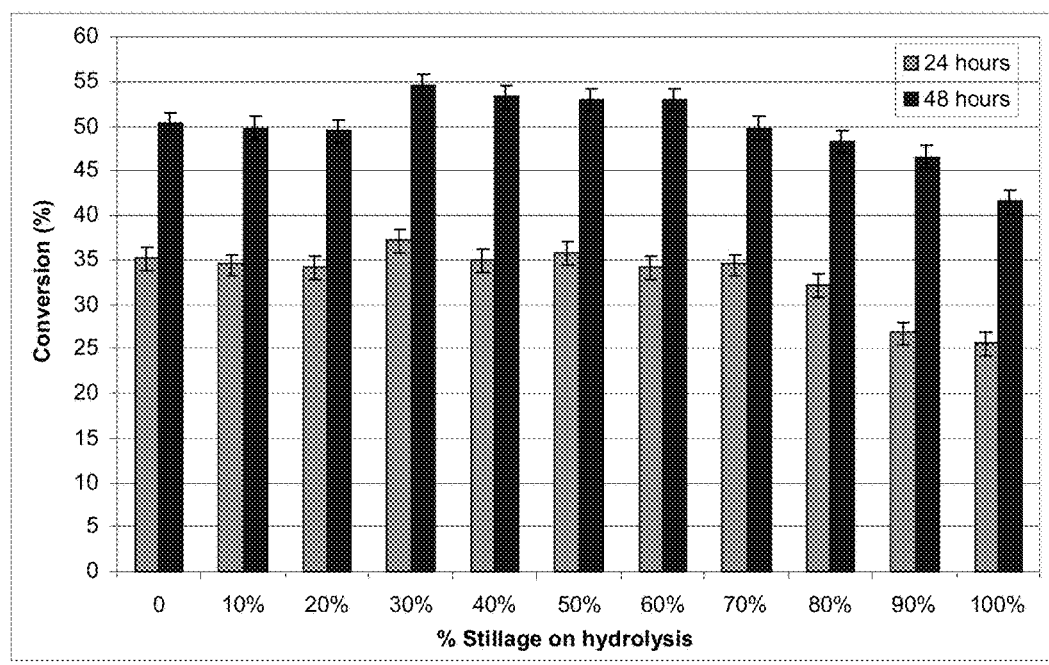

FIG. 7 is the enzymatic hydrolysis of sugarcane bagasse pretreated by the steam explosion having different concentrations of stillage in the reaction medium.

DETAILED DESCRIPTION OF THE INVENTION

Examples shown here are only intended to exemplify some of the many ways to carry out the invention without limiting the scope thereof.

Lignocellulosic Vegetal Biomass

The expression lignocellulosic vegetal biomass comprises any type of plant, that is: herbaceous biomass; cultivars such as plants C4—from genera *Lolium, Spartina, Panicum, Miscanthus*, and combinations thereof; sugar cane bagasse (from the mill and/or diffuser); sugar cane straw; cereal straw such as wheat, rice, rye, barley, oat, maize and the similar (e.g. switchgrass); wood, trunks and sticks of banana trees; cactuses and combinations thereof. In addition, lignocellulosic materials can also comprise cardboard, sawdust, newspaper and agroindustrial or municipal waste and the similar.

Vegetal biomasses from different origins can present particular differences, although they own a relatively similar global chemical composition. Some variations in the composition among different species and inside the same species are due to the environmental and genetic variabilities, despite the localization of the vegetal tissue in different parts of the plant. Typically, lignocellulosic biomasses present from 35% to 50% of cellulose, from 20% to 35% of hemicellulose and from 20% to 30% of lignin. In addition to these majority fractions, there are still minority amounts of ashes, phenolic compounds, organic acids and compounds called extractives. Cellulose and hemicelluloses of the vegetal tissue are constituted by structural carbohydrates (e.g. glycans, xylans, manans) and they are in general called saccharide fraction. Lignin, on the other hand, represents the phenolic fraction of the vegetal biomass.

Stillage

In the present invention, it is understood as stillage any residue from the distillation process of wine without yeasts, obtained after fermentation and separation of yeast cells, generally by centrifugation, but not limited to it.

Buffering Agent

In chemistry, buffer solutions are solutions that can mitigate variations in pH, stabilizing it at a relatively constant value, even if the system suffers disruption by adding acids or bases.

The stillage obtained in the present invention, for its high concentration of ions such as sodium, is able to react with the acids generated in the pretreatment process/hydrolysis, then maintaining the pH of the medium in a constant range and favorable for enzyme activity.

The stillage of the present invention is very useful in enzymatic hydrolysis processes in general, but specially in saccharification reactions of lignocellulosic biomasses.

The stillage of the present invention, being a byproduct of fermentation, presents low cost and replaces commonly used quite efficiently buffering agents having low cost such as, for example, citric acid.

The buffering agent is produced by a process comprising the step of collecting a stillage produced in the distillation process of wine without yeasts, resulting from the alcoholic fermentation process, and, optionally, filtering, evaporating and/or concentrating it.

Enzymatic Hydrolysis Process

The enzymatic hydrolysis process of the present invention is a process comprising the addition of any amount of stillage to the reaction medium in order to provide its buffering.

In a preferred embodiment, the hydrolysis process is a saccharification process and can occur under any configuration known by the state of the art, and selected from the group comprising SHF (separated Enzymatic hydrolysis and Fermentation), SSF (Simultaneous Enzymatic hydrolysis and Fermentation), SSCF (Simultaneous Enzymatic hydrolysis, Simultaneous Fermentation and Co-Fermentation), CBP (Enzyme production, Enzymatic hydrolysis and Simultaneous Fermentation), SEPHY (Enzyme production and Enzymatic hydrolysis separated from the Fermentation) and combinations thereof.

Fermentation Additive

The fermentation additive of the present invention is a solution rich in nitrogen, essential nutrient for growing microorganisms responsible for the fermentation, even if they are yeasts or bacteria.

The stillage obtained in the present invention, for its high concentration of nitrogen, serves as an additional nutritional source in the fermentation process. Thus, the stillage of the present invention is very useful in the fermentation process in general and in special in alcoholic fermentation reactions.

The fermentation additive is produced by a process comprising the step of collecting a stillage produced in the distillation process of wine without yeasts, resulting from the alcoholic fermentation process, and, optionally, filtering, evaporating and/or concentrating it.

Fermentation Process

The fermentation process of the present invention encompasses any fermentation process, whether bacterial or by means of yeasts, comprising a step of fermentation in the presence of a fermentation additive made of stillage.

In a preferred embodiment, the fermentation process of the present invention aims to obtain ethanol.

EXAMPLE 1

Materials and Methods

Lignocellulosic Material: Bagasse typical of sugar cane (humidity of approximately 50%) was collected in an alcohol and sugar mill and located in Piracicaba/SP, immediately after sugar cane milling (fresh bagasse).

Pretreatment with Steam explosion: Sugarcane bagasse "in natura" was pretreated with vapor (Steam Explosion) aiming to promote chemical and structural changes in the biomass, aiming to obtain a substrate (pulp) having a high cellulose content and high accessibility of the matrix Lignin-carbohydrate to cellulolytic enzymes. In this sense, effective processes are characterized by high removal of hemicelluloses and selective extraction of xylose (monomer and oligomer), having minimal glucose removal. Furthermore, such processes must produce minimum of compounds inhibiting enzymatic action (e.g. furfural, HMF, humic acids and phenolic derivatives), produced from the breakdown of carbohydrates and of lignin.

Pretreatment experiments with vapor were performed in the offices of CTC (Sugarcane Research Center, Piracicaba/SP) and, in general, in a single step. In FIG. 6 a schematic drawing is presented of the apparatuses used, consisting essentially of a 65 L-reactor (pretreatment reactor or hydrolyser) coupled by a tube with an expansion tank (flash tank) like a cyclone. The reactor was charged with bagasse from the mill and/or diffuser collected in alcohol and sugar mills of the state of São Paulo, under typical conditions. Generated vapor by the 30 kgf/cm$^2$ boiler was directly injected in the reactor by opening valves. The heating curve and the pressure recording in the reactor were manually monitored. After the residence time being determined, the reactor was discharged, by sudden decompression or via ramp decompression, and the pretreated material (slurry) collected in the expansion tank after system pressure relief and releasing of the produced vapor. The obtained pretreated bagasse showed characteristics which gave it the power of a feedstock for the enzyme production and enzymatic hydrolysis, for the production of bioethanol from bagasse.

Characterization of Pretreated bagasse: Sugar cane bagasse "in natura" and pretreated with steam explosion were characterized for its main constituents (structural carbohydrates and lignin), following the experimental methodology based on the protocol designed by National Renewable Energy Laboratories (NREL), United States of America (Sluiter et. al., 2004).

The characterization of these materials requires the determination of the humidity content, using differential gravimetry in electronic scale after greenhouse for measuring the percentage in relation to the dry base of the material. For the determination of insoluble lignin content in acid and structural carbohydrates a sample of dry bagasse was mixed to H$_2$SO$_4$ (72%), under agitation for 1 hour. The reaction was stopped by the addition of distilled water. Next, for the complete hydrolysis of the remaining oligomers, the suspension was autoclaved (121° C.) for 1 hour. The liquid fraction (hydrolysate) was used for determining structural carbohydrates by liquid chromatography (HPLC) and the solid fraction was washed with distilled water and dried in greenhouse (105° C.) for subsequent calcination (575° C.) and determination of lignin by gravimetry.

The determination of structural carbohydrates by HPLC was done using the refractive index detector (IR), using external patterns for each component, column Aminex HPX 87H (300×7.8 mm, BIO-RAD) and mobile phase 5 mM H$_2$SO$_4$ having a flow rate of 0.6 mL/min at 45° C.

Enzymatic hydrolysis: Pretreated sugarcane bagasse was subjected to enzymatic hydrolysis using different concentrations of industrial stillage which was typical in the reaction medium, according to Table 1 below. In parallel, experiments in the absence of stillage, herein called reference experiments, were also performed under identical experimental conditions:

TABLE 1

Enzymatic hydrolysis

| Experiment | Relation % Stillage/% Water |
| --- | --- |
| 1 | 10%-90% |
| 2 | 20%-80% |
| 3 | 30%-70% |
| 4 | 40%-60% |
| 5 | 50%-50% |
| 6 | 60%-40% |
| 7 | 70%-30% |
| 8 | 80%-20% |
| 9 | 90%-10% |
| 10 | 100%-0% |

The experiments of enzymatic hydrolysis were performed in a 60 L-reactor, under the following experiment conditions: 50° C.; pH 4.8-5.2; 8% of total solids; the enzyme load of 13.5 mL of enzyme/kg of dried bagasse and 48 hours of reaction. The reactions of hydrolysis were conducted using the enzyme Cellic Ctec 2, given by Novozymes® (Novozymes Latin America Ltda.—Araucaria/PR, Brazil). The conversion of cellulose present in the biomass in glucose (fermentable sugar) reached in each test conducted was calculated by the following equation (1):

$$\eta = \frac{M_{Experimental\ glucose} - M_{Blank}}{M_{Cellulose} * 1.111} * 100\% \quad (1)$$

wherein: $M_{Experimental\ glucose}$ is the glucose mass present in the hydrolysate broth after 48 hours of reaction; $M_{blank}$ is the glucose mass measured in the essay performed under identical experimental conditions, but in the absence of enzymes; $M_{Cellulose}$ is the initial mass of cellulose present in the pretreated bagasse and 1,111 is the conversion factor from cellulose to glucose.

EXAMPLE 2

Pretreated bagasse Composition: The bagasse composition pretreated with steam explosion was determined using the experimental methodology based on the procedure designed by NREL, as previously described, and it is shown in Table 2 as follows:

TABLE 2

Bagasse Composition pretreated with steam explosion (dry base) in relation to its majorities fractions.

| Pretreated bagasse | Percentage in dry base |
| --- | --- |
| Humidity | 65.42% |
| Dry solids | 34.58% |
| Cellulose | 59.20% |
| Hemicellulose | 2.80% |
| Lignin | 33.30% |
| Soluble solids | 17.50% |
| Insoluble solids | 82.50% |

As it can be seen in the above table, the treatment with vapor preserved the cellulose and lignin fractions and significantly solubilized a hemicellulose, as desired. Thus, it is expected that the accessibility of the enzymes to their specific substrates become considerably easier in the pretreated bagasse.

EXAMPLE 3

Enzymatic hydrolysis of cellulose having solids load of 8%: In all experiments performed in the presence of stillage, the final set of reactional suspension pH was done with sodium hydroxide (NaOH). Experiments with hydrolysis in the absence of stillage and the so called here "reference" were performed in triplicate, using buffer solutions sodium citrate 50 mM, pH 5. FIG. 7 shows the conversion obtained.

As it can be observed in FIG. 7, the concentration range of stillage which allows high conversions from cellulose to glucose to be reached in the period of 48 hours is from 30% to 60%. Such final values are even higher than those observed for the reference essay, which indicates that the presence of the stillage not only does not cause any kind of inhibition in the used enzymes, but also provides a hydrolysate broth much more suitable for the next step of fermentation, due to the presence of typically found in the stillage.

Those skilled in the art will value the teachings presented here and they will be able to reproduce the invention in the presented embodiments and in other variants, within the scope of the appended claims.

The invention claimed is:

1. An enzymatic hydrolysis process comprising adding stillage as a buffering agent to a reaction medium containing lignocellulosic vegetal biomass, wherein said lignocellulosic vegetal biomass is selected from the group consisting of sugar cane bagasse, sugar cane straw, and a mixture of sugar cane bagasse and sugar cane straw, wherein the stillage is added in an amount that varies, in mass percentage (% w/w), from 30% to 60% and the amount of water varies, in mass percentage (% w/w), from 70% to 40%, and wherein a pH range from 4.5 to 5.5 is maintained.

2. The process according to claim 1, wherein the stillage is a residue derived from a distillation process of wine without yeasts, obtained after fermentation and separation of yeast cells.

3. The process according to claim 2, further comprising filtering, evaporating, or concentrating the stillage before adding the stillage as a buffering agent to the reaction medium.

* * * * *